(12) United States Patent
Dozier et al.

(10) Patent No.: US 7,135,606 B1
(45) Date of Patent: Nov. 14, 2006

(54) WOUND DRESSING

(76) Inventors: Terrance Dozier, 2620 Lakeshore Dr., Macon, GA (US) 31202; Glenda Dozier, 2620 Lakeshore Dr., Macon, GA (US) 31202

( * ) Notice: Subject to any disclaimer, the term of this patent is extended or adjusted under 35 U.S.C. 154(b) by 0 days.

(21) Appl. No.: 10/890,903

(22) Filed: Jul. 15, 2004

(51) Int. Cl.
*A61F 13/00* (2006.01)

(52) U.S. Cl. ............... 602/57; 602/54; 602/55; 602/56

(58) Field of Classification Search ............... 128/893, 128/894, 888, 890, 889, 898; 602/41–43, 602/57, 54, 55, 56; D24/189
See application file for complete search history.

(56) References Cited

U.S. PATENT DOCUMENTS

| | | | |
|---|---|---|---|
| 4,641,643 A * | 2/1987 | Greer | ............... 128/888 |
| 4,917,112 A | 4/1990 | Kalt | |
| 5,060,662 A * | 10/1991 | Farnswoth, III | ............ 128/888 |
| 5,086,764 A | 2/1992 | Gilman | |
| 5,180,360 A | 1/1993 | Rhame, Jr. | |
| 5,722,943 A | 3/1998 | Sessions | |
| 5,743,272 A * | 4/1998 | Kocher, Jr. | ................. 128/846 |
| 5,998,694 A * | 12/1999 | Jensen et al. | ................. 602/57 |
| 6,120,792 A | 9/2000 | Juni | |
| 6,436,432 B1 | 8/2002 | Heinecke et al. | |
| 6,465,708 B1 * | 10/2002 | Augustine | ................... 602/42 |
| 6,607,799 B1 | 8/2003 | Heinecke et al. | |

* cited by examiner

*Primary Examiner*—Henry Bennett
*Assistant Examiner*—Camtu Nguyen
(74) *Attorney, Agent, or Firm*—Harpman & Harpman

(57) ABSTRACT

A wound dressing bandage having an integral support and adhesive carrying body with a central absorbent dressing pad for positioning over a skin wound. The support and adhesive body member has a tough flexible resilient sheet defining a perimeter band about the dressing pad. An engagement tab extends beyond the perimeter for frangible release and removal of the release sheet during application.

5 Claims, 3 Drawing Sheets

WOUND DRESSING

BACKGROUND OF THE INVENTION

1. Technical Field

This invention relates to wound dressings and self-adhesive bandages that are used to selectively cover skin wounds. Such adhesive bandages combine a sterile absorbent pad with an adhesive caring sheet with release sheets thereon.

2. Description of Prior Art

Prior art devices of this type have been directed to a variety of different structural designs in which adhesive strips of flexible synthetic material are combined with a pre-positioned gauze absorbent sterile pad to be placed directly over the skin wound adhering to the surrounding area so as to prevent environmental matter from coming in direct contact with the wound until it is healed. Such devices can be seen in U.S. Pat. Nos. 4,917,112, 5,086,764, 5,180,360, 5,722,943, 6,120,792, 6,436,432, and 6,607,799.

U.S. Pat. No. 4,212,996 is directed to a bandage with a protective member having a central pad portion with oppositely disposed end extensions for adhesively securing the bandage to the patient.

U.S. Pat. No. 4,917,112 discloses a bandage with a transparent dressing area surrounded by an adhesive surface.

U.S. Pat. No. 5,086,764 claims an absorbent dressing having wound covering base with an absorbing fabric wound engagement area therewithin.

U.S. Pat. No. 5,180,360 is directed to an eye patch with a central inflatable bladder to maintain the eyelid in closed position once it is positioned on the patient.

U.S. Pat. No. 5,722,943 is non-stretching wound dressing having multiple positioning and release sheets configurations and a process for manufacturing same.

U.S. Pat. No. 6,120,792 shows a medicated skin patch and use method which utilizes several alternate forms having different shape configurations.

U.S. Pat. No. 6,436,432 is an absorbent pad dressing frame with the pad on a carrier frame having multiple overlapping structural layers thereon.

U.S. Pat. No. 6,607,799 illustrates a surgical dressing with delivery system and manufacturing method. A would dressing is shown having multiple layer hinge configuration for positioning of a catheter in a patient.

Pat. No. D265,423 discloses an I.V. bandage having an upper access flap and applicant's own U.S. Pat. No. D372,787 shows integral circular bandage configuration with a central raised absorbent pad compartment with a pair of overlapping tab extensions extending therefrom.

SUMMARY OF THE INVENTION

A wound dressing having a central recess portion with an absorbent pad within. An integral overlying securing surface and ring defines the recess central area with an adhesive band thereon having a frangible release cover sheet. The wound dressing can be positioned over a skin puncture and held in place initially while the adhesive release sheet is then removed adhering the dressing onto the skin about the wound.

DESCRIPTION OF THE PREFERRED EMBODIMENT

Figure 1:
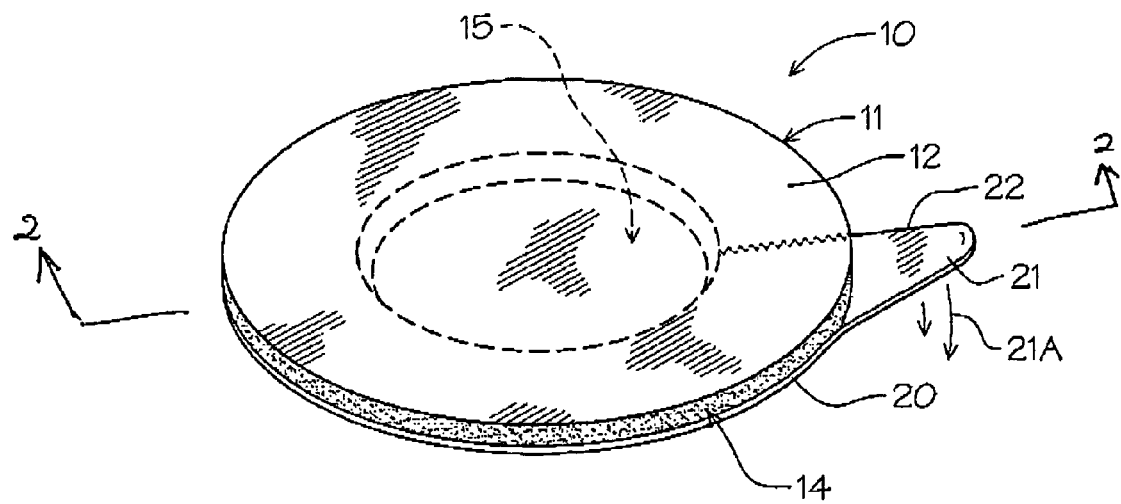
FIG. 1 is a perspective view of the wound dressing of the invention.
Figure 2:
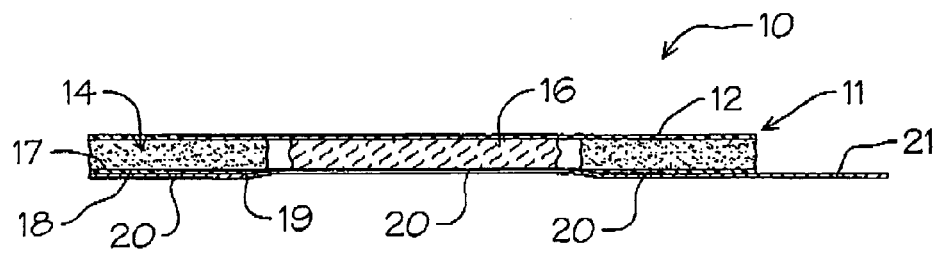
FIG. 2 is a cross-sectional view on lines 2—2 of FIG. 1.
Figure 3:
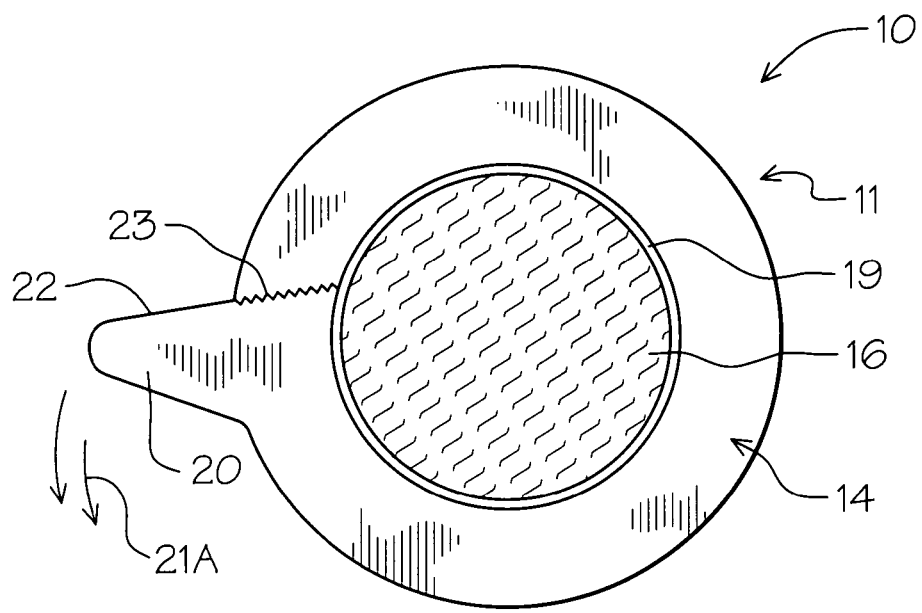
FIG. 3 is a bottom plan view of the wound dressing.
Figure 4:
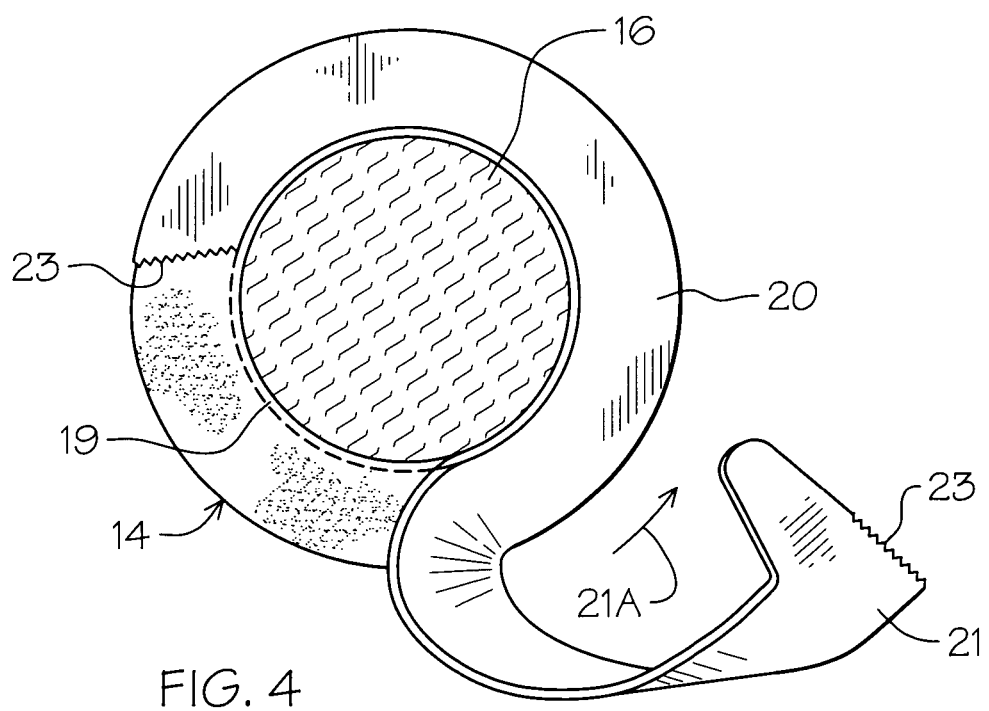
FIG. 4 is a bottom plan view of the wound dressing with a portion of the release strip removed.

Referring to FIGS. 1–3 of the drawings, a wound dressing 10 of the invention can be seen having a main support and enclosure body member 11 defining a circular configuration with an integral top surface 12. The body member 11 defines a raised annular band 14 with a central recessed area 15 within. The top surface 12 overlies the recessed area 15 providing a capture support for a sterile absorbent material pad 16 positioned within. The bottom surface 17 of the annular band 14 has a pressure sensitive adhesive coating 18 thereon. It will be noted that the sterile material pad 16 is of overall dimension less than that of the recessed area 15 with an adjacent inner perimeter edge having no adhesive covering as indicated at 19. This arrangement assures that there will be no inter-engagement of the pad with the adhesive and provides an isolated field about the wound and the pad 16.

A specialized release sheet 20 overlies the adhesive coating 18 on the bottom surface 17 of the annular band 14 having an engagement tab 21 extending outwardly therefrom in planar relationship thereto. The engagement tab 21 has a leading edge 22 from which extends a perforation line 23 within the release sheet 20 extending transversely across the corresponding portion of the annular band 14 adjacent thereto. The perforation line 23 will provide a frangible separation of the release sheet 20 upon engagement of the tab 21 by the user (not shown) and appropriately applied trans-lateral force indicated by directional arrows 21A during removal which will be discussed in greater detail hereinafter.

Figure 5:
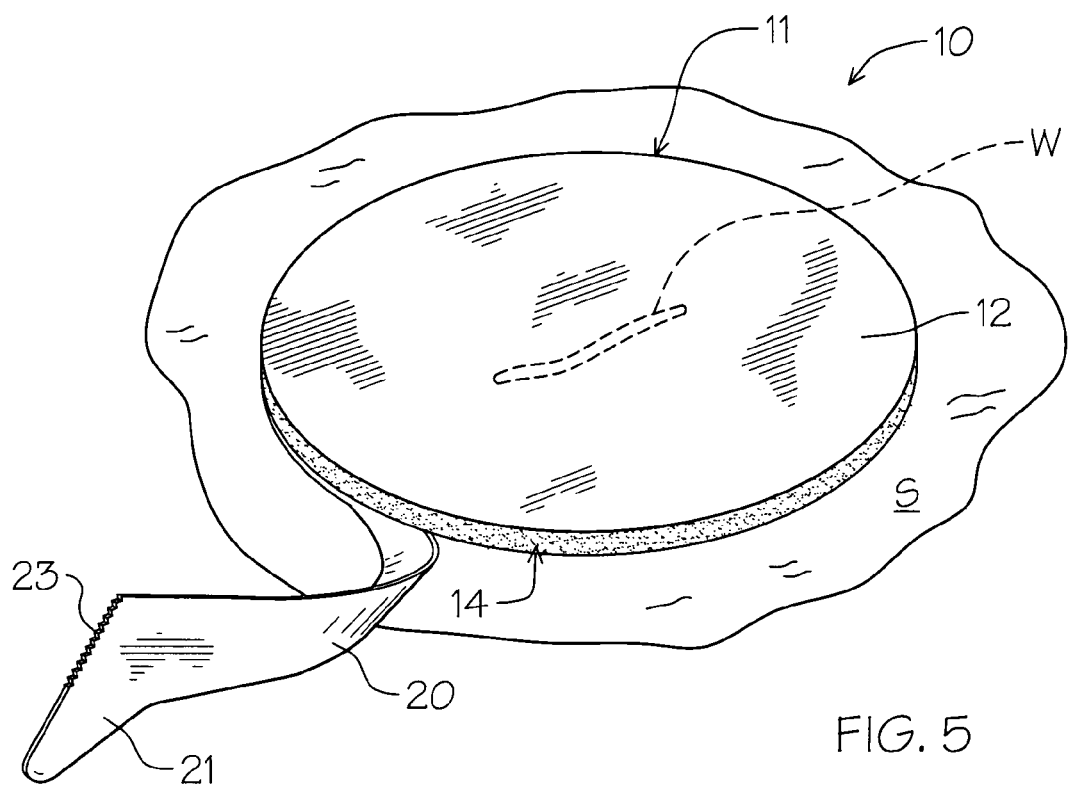
FIG. 5 is a perspective view of the wound dressing during use as the release sheet is removed once in place.
Figure 6:
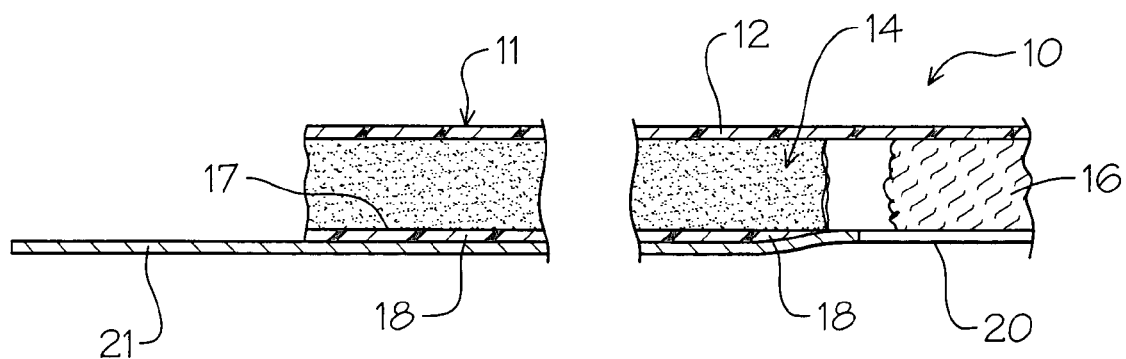
FIG. 6 is a partial sectional view of the wound dressing.

The main support and enclosure frame 11 as noted defines the raised annular base band 14 which is preferably composed of a synthetic resin base material having an expanded foam or fabric of properties so has to be lightweight and compressible for flexible contouring to the applied skin S area as illustrated in FIG. 5 of the drawings during application and the duration of its in place use.

It will be noted that relative thickness of the annular base band 14 is proportional to that of the required use venues and therefore can vary depending on the relative thickness of the pad 16 to be used in treating different wound configurations. The primary or preferred form is of a dimensional thickness sufficient to form the hereinbefore described recess area 15 with the integral overlying top surface 12 being co-planar with that of the perimeter upper edge surfaces of the annular band 14.

The wound dressing 10 of the invention would be typically stored in a sterile disposable enclosure (not shown) and once removed therefrom would be placed centrally over the wound W, as illustrated in FIG. 5 of the drawings. The wound dressing 10 so placed would position the infilled absorbent material pad 16 such as a sterile cotton or gauze directly over the wound W. With pressure then being applied by the user to the wound dressing 10 to hold same in place, the user then grasps the tab 21 and pulls upwardly and trans-laterally in a spiral annular configuration severing the frangible perforation line 23 allowing the release sheet 20 to be pulled thereabout and outwardly from under the bottom surface 17 of the raised annular band portion 14 defined by the enclosed body member 11. Simultaneously exposing the adhesive coating 18 to the user's skin S there beneath for adhesion.

This allows for a simple and effective placement and deployment of the wound dressing 10 of the invention, taking advantage of the unique support and enclosure frame 11 and integral frangible release sheet 20 as hereinbefore described.

It will thus be seen that a new and novel wound dressing has been illustrated and described and it will be apparent to those skilled in the art that various changes and modifications may be made thereto without departing from the spirit of the invention.

We claim:

1. A dressing for a wound comprising,
   a main support body member for placement on a user's skin surrounding the wound, said main support body member of a three-dimensional configuration defining a central recess area overlying the wound,
   an integral top surface on said main support body member overlying said central recess area therein,
   a sterile absorbent pad positioned within said recess area infilling the majority of the recess area and overlying the wound,
   said sterile absorbent pad defining a circular wound engagement surface,
   an adhesive coating on an annular skin engagement surface of said main support body member,
   a release sheet overlying said adhesive coating and extending therefrom,
   an integral engagement tab on said release sheet and a frangible perforation line extending from said tab across an adjacent release sheet portion adjacent thereto transecting and separating the annular surface into an elongated band for progressive removal from said annular skin engagement surface.

2. The wound dressing set forth in claim 1 wherein a portion of said integral top surface overlying said central recess area is co-planar with said remaining portion thereabout.

3. The wound dressing set forth in claim 1 wherein said central recess area defined by said main support body member is of a known annular dimension and said absorbent pad is a known annular dimension less than that of said central recess area.

4. The wound dressing set forth in claim 1 wherein said adhesive coating on said main supporting body member's annular skin engagement surface extends from the perimeter edge thereof to a point in spaced annular relation to said sterile absorbent pad.

5. The wound dressing set forth in claim 1 wherein said main support body member is of a compressible flexible synthetic material.

* * * * *